United States Patent [19]

Nakano et al.

[11] Patent Number: 4,999,196
[45] Date of Patent: Mar. 12, 1991

[54] COMPOUND DC-107 PRODUCED BY STREPTOMYCES SP.

[75] Inventors: Hirofumi Nakano; Mitsunobu Hara; Isami Takahashi, all of Machida; Kozo Asano, Tsukuba; Takao Iida, Tama; Makoto Morimoto, Shizuoka, all of Japan

[73] Assignee: Kyowa Hakko Kogyo Co., Ltd., Tokyo, Japan

[21] Appl. No.: 330,990

[22] Filed: Mar. 29, 1989

Related U.S. Application Data

[63] Continuation-in-part of Ser. No. 218,923, Jul. 14, 1988, abandoned.

[30] Foreign Application Priority Data

Jul. 22, 1987 [JP] Japan .................. 62-182867
Feb. 19, 1988 [JP] Japan .................. 63-36525

[51] Int. Cl.$^5$ .................. A61K 31/12; C12P 7/22; C12P 7/26; C12P 1/04
[52] U.S. Cl. .................. 424/116; 424/117; 424/118; 435/128; 435/130; 435/132; 435/886
[58] Field of Search .................. 424/116, 117, 118; 435/128, 130, 132, 886

[56] References Cited

U.S. PATENT DOCUMENTS

| 3,812,096 | 5/1974 | Argoudelis et al. | 435/886 |
| 3,817,979 | 6/1974 | Argoudelis et al. | 435/886 |
| 3,907,774 | 9/1975 | Argoudelis et al. | 435/886 |
| 3,988,441 | 10/1976 | Hanka et al. | 435/886 |

OTHER PUBLICATIONS

Hara et al., The Journal of Antibiotics, vol. XLII, No. 2, pp. 333–335 (1989).
Blumauerova et al., Chemical Abstracts, vol. 89, pp. 293–294, abstract no. 176175n (1978).
Gurevich et al., Chemical Abstracts, vol. 68, pp. 2375, abstract no. 24522b (1968).

Primary Examiner—Robert A. Wax
Assistant Examiner—Stephanie W. Zitomer
Attorney, Agent, or Firm—Fitzpatrick, Cella, Harper & Scinto

[57] ABSTRACT

A novel compound, DC-107, is produced by culturing a microorganism belonging to the genus Streptomyces. It is useful as a medicine because of its antibacterial and anti-tumor activity.

5 Claims, 4 Drawing Sheets

COMPOUND DC-107 PRODUCED BY STREPTOMYCES SP.

This application is a continuation-in-part of application Ser. No. 218,923 filed July 14, 1988, now abandoned.

BACKGROUND OF THE INVENTION

The present invention relates to the novel compound DC-107 and a process for preparing the same. DC-107 has antibacterial and anti-tumor activity.

Many compounds such as anthracycline compounds, anthraquinone compounds and mitomycin compounds have been hitherto reported as anti-tumor antibiotics (CRC Handbook of Antibiotic Compounds, 1981, CRC Press, U.S.A).

Mitomycin C, adriamycin, bleomycin, etc. are known as anti-tumor antibiotics used in chemotherapy of tumor. However, there has been a constant demand for substances having a further excellent anti-tumor activity in view of the problems of resistance cancers for which these drugs are ineffective, and the like.

The present inventors have found that the compound DC-107 obtained by culturing a strain belonging to the genus Streptomyces has excellent antibacterial and anti-tumor activity.

Physicochemical properties of DC-107 indicate that the compound does not belong to any of the above groups of known compounds. Further, it is also clear from the molecular formula of DC-107, $C_{22}H_{26}N_2O_6S_3$, that the compound is a novel compound.

SUMMARY OF THE INVENTION

In accordance with the present invention, the novel compound DC-107 is produced by culturing a microorganism belonging to the genus Streptomyces which is capable of producing DC-107 in a medium. DC-107 has antibacterial and anti-tumor activity.

DETAILED DESCRIPTION OF THE INVENTION

The present invention provides the novel compound DC-107 having antibacterial and anti-tumor activity. The compound is characterized by the following physicochemical properties:

(1) Molecular formula: $C_{22}H_{26}N_2O_6S_3$ (2) Molecular weight: 510, Found by high resolution FAB mass spectrum: 511.1041, Calculated for $C_{22}H_{27}N_2O_6S_3$: 511.1031, (3) Melting point: 160° C. (decomposed)

(4) Specific rotation:

$[\alpha]^{25}_D = 140°$ (c=0.1, methanol)

Figure 1:
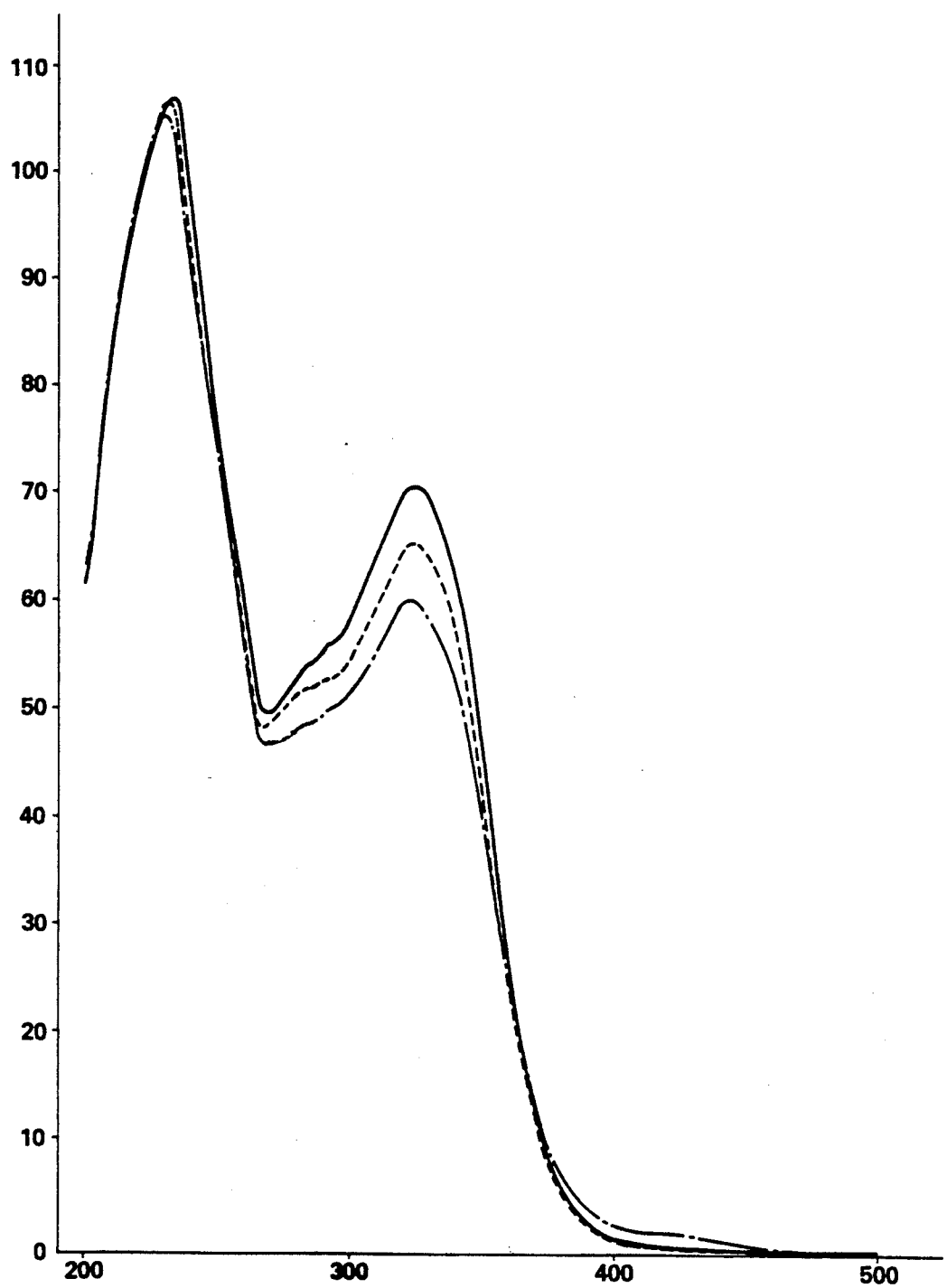
FIG. 1 shows the UV absorption spectra of DC-107 in methanol, in which the solid line represents the data under neutral conditions, the broken line the data under acidic conditions (0.01N HCl), and the alternate long and short dash line the data under alkaline conditions (0.01N NaOH).

(5) Ultraviolet absorption spectrum: As shown in FIG. 1

Figure 2:
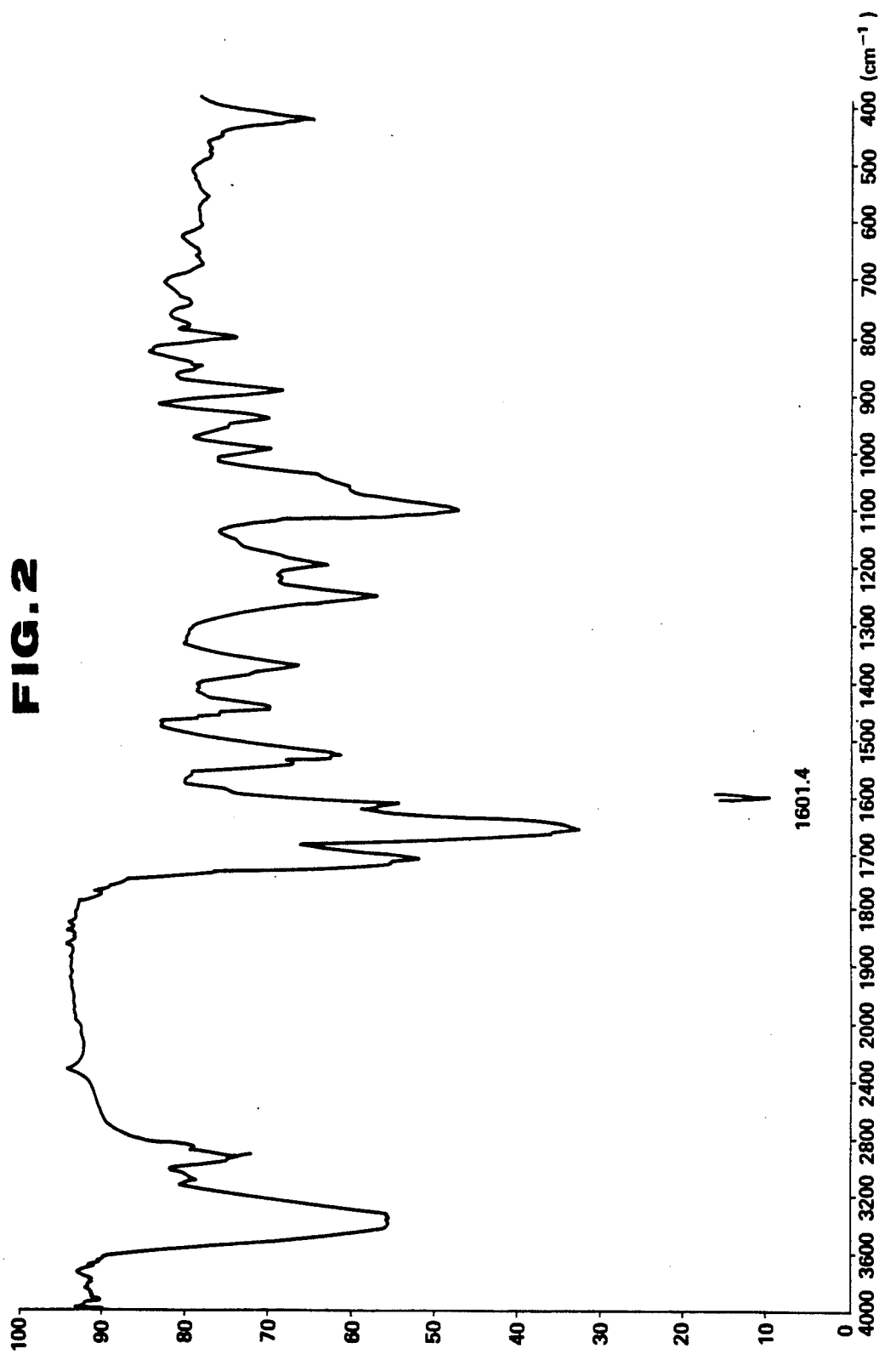
FIG. 2 shows the IR absorption spectrum of DC-107 by the KBr method.

(6) Infrared absorption spectrum: As shown in FIG. 2

(7) Solubility: Soluble in methanol, ethyl acetate, chloroform and acetone, Insoluble in water and n-hexane (8) Color reaction:

Positive in reactions with ninhydrin, p-anisidine and Ehrlich's reagent (9) A white, neutral substance

Figure 3:
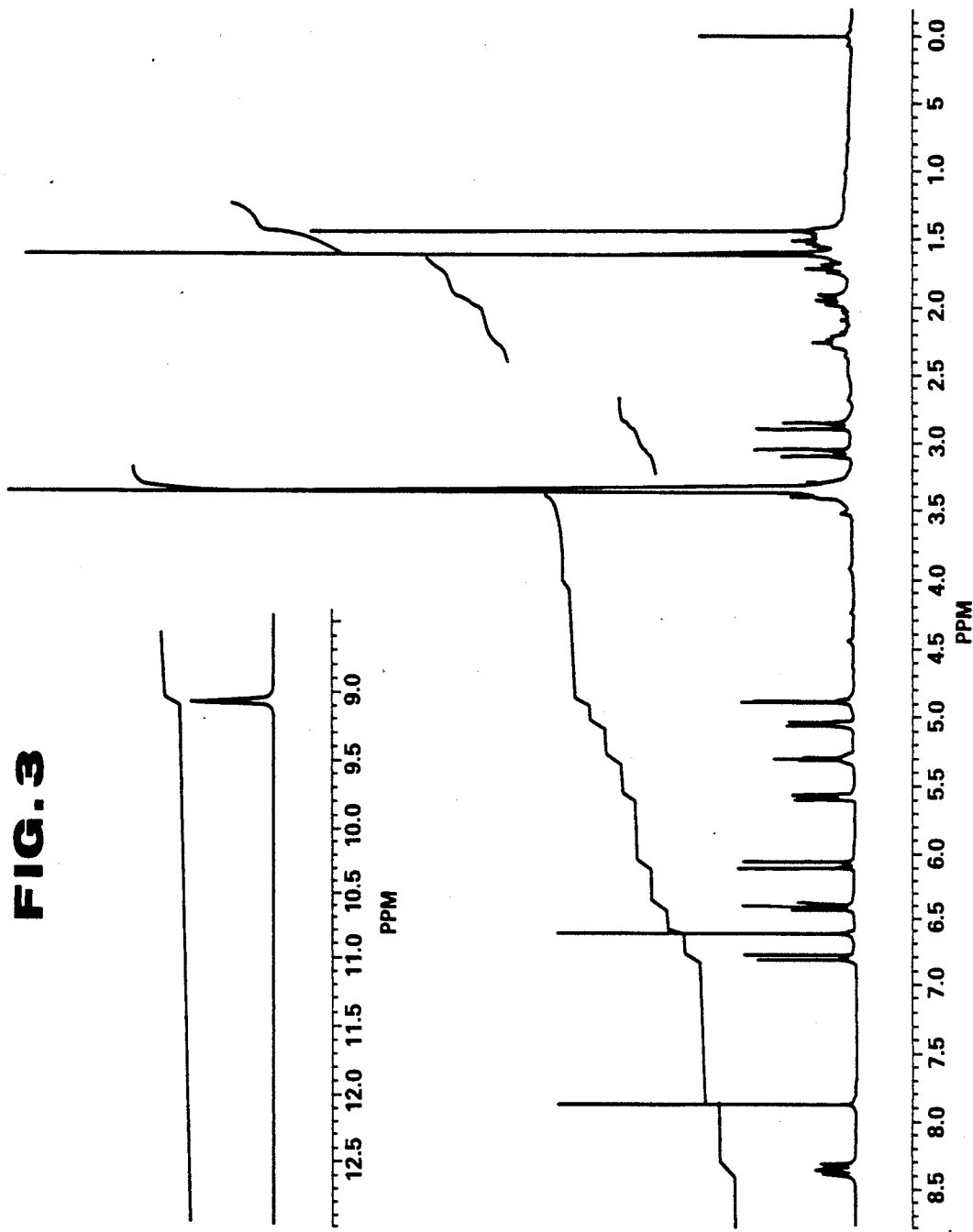
FIG. 3 shows the 400 MHz $^1$H-NMR spectrum of DC-107 obtained using DMSO-$d_6$ as the solvent and tetramethylsilan (TMS) as the internal standard.

(10) $^1$H-NMR spectrum (400 MHz, in DMSO-$d_6$, internal standard TMS) As shown in FIG. 3

Figure 4:
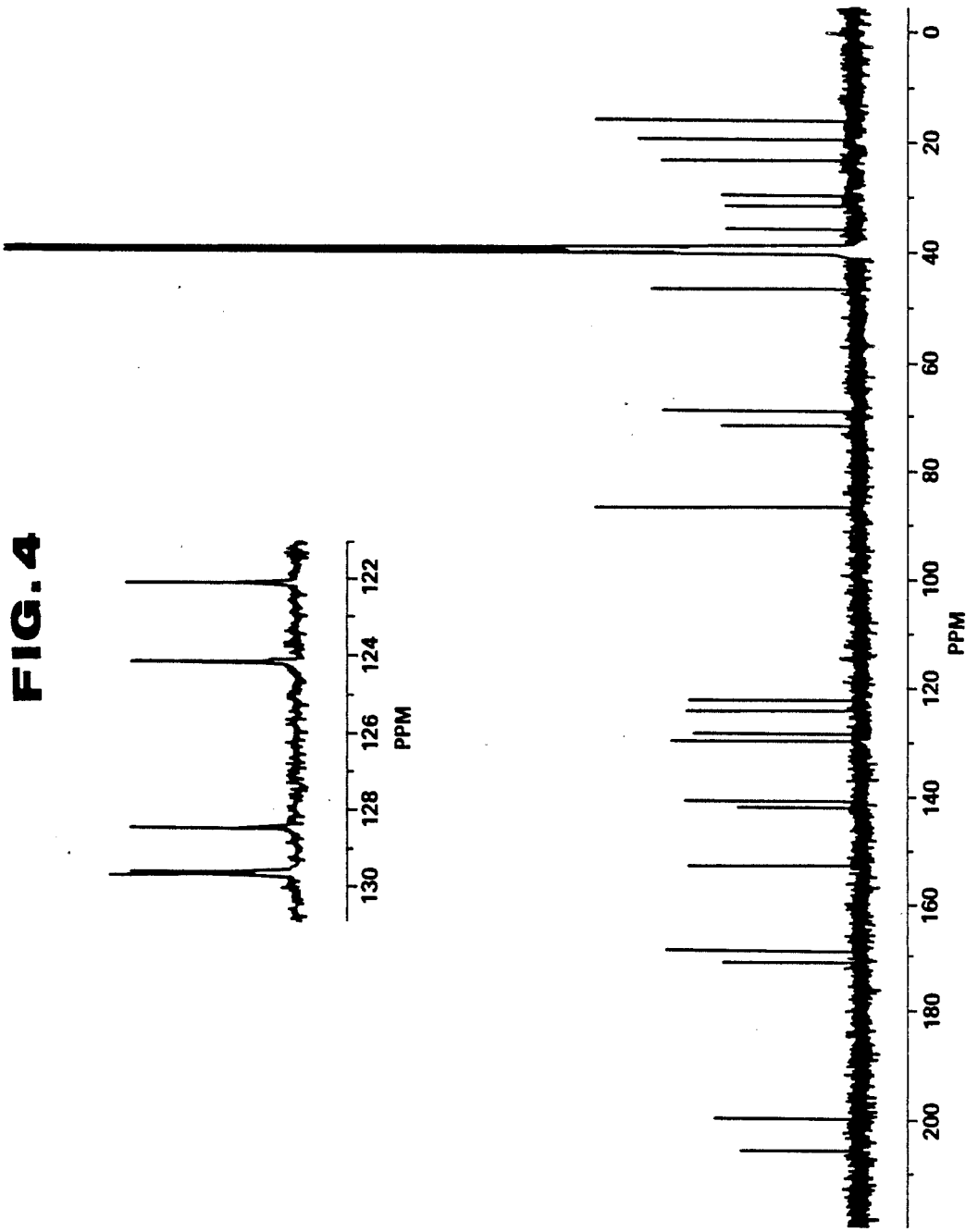
FIG. 4 shows the 100 MHz $^{13}$C-NMR spectrum of DC-107 obtained using DMSO-$d_6$ as the solvent and tetramethylsilan (TMS) as the internal standard.

(11) $^{13}$C-NMR spectrum (100 MHz, in DMSO-$d_6$, internal standard TMS) As shown in FIG. 4

(12) Thin layer chromatography: Table 1 shows the $R_f$ values when DC-107 is chromatographed on silica gel (Kieselgel 60 Art. 5715; Merck, West Germany) and developed with various solvent systems at room temperature for one hour.

TABLE 1

| Solvent system | $R_f$ |
|---|---|
| Chloroform:methanol (20:1) | 0.40 |
| Ethyl acetate | 0.80 |
| n-Hexane:ethyl acetate:acetic acid (5:5:0.1) | 0.15 |

The structure of DC-107 is characterized by X-ray structural analysis. According to this method of analysis, colorless, needle-like crystals were grown from a $CH_2Cl_2$: $CHCl_3 = 3:10$ solution by slow evaporation. The maximum size of the crystals is ca. $0.5 \times 0.3 \times 0.2$ mm., and the calculated density is 1.34 g/cm$^3$. There are a few solvent molecules, i.e. $CH_2Cl_2$ and $CHCl_3$ molecules, in the crystal. The crystal data are as follows: monoclinic, space group C2, a=23.99(1), b=11.369(5), c=22.766(5) Å, $\beta$=99.12(4)° and Z=4. It is thus determined that there are two molecules in an asymmetric unit. A four-circle diffractometer was used to collect the intensity data by sue of Cu K$\alpha$ radiation ($\lambda$=1.54184 Å) from a rotating anode X-ray generator. The crystals are rapidly decayed by X-ray radiation, and 1740 reflections [$I \geq \sigma(I)$] were observed. DC-107 has been assigned the following structure using direct methods refined by full-matrix least-squared refinement.

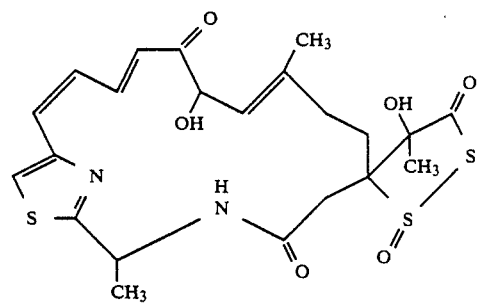

In this regard, it is understood that X-ray analysis (wherein X-ray beams diffracted from a crystal are characterized by an amplitude proportional to the square root of the intensity and by a phase angle) is intended to locate all the atoms in a crystal lattice. However, although amplitudes can be measured experimentally using x-ray all the atoms in a crystal lattice. However, although amplitudes can be measured experimentally using x-ray analysis, it is not possible to obtain the phase information by experiment, without which information the atoms can not be located. Therefore, it is necessary to estimate the phase angles. In the direct methods technique, the phase angles are mathematically estimated utilizing phase information contained in the distribution of intensities of diffracted beams. Such methods do not require prior phase information and, when they are successfully applied, automatically yield the phase angles.

Biological properties of DC-107 are shown below.

(A) Antibacterial activity

The antibacterial activity was determined by the agar dilution method using a medium (pH 7) prepared by dissolving 3 g of Bacto-Tryptone (Difco Laboratories), 3 g of meat extract, 1 g of yeast extract, 1 g of glucose and 16 g of agar in 1 liter of water. The result is shown in Table 2.

TABLE 2

| Bacteria Tested | Minimum Inhibitory Concentration (µg/ml) |
|---|---|
| Staphylococcus aureus ATCC 6538P | 1.6 |
| Bacillus subtilis No. 10707 | 0.08 |
| Klebsiella pneumoniae ATCC 10031 | 1.6 |
| Escherichia coli ATCC 26 | 2.6 |
| Shigella sonnei ATCC 9290 | 10.4 |
| Salmonella typhi ATCC 9992 | 20.8 |

(B) Acute toxicity

The acute toxicity value ($LD_{50}$) was about 5 mg/kg when DC-107 was intraperitoneally administered to mice.

(C) Anti-tumor activity (1) Therapeutical effect against Sarcoma 180 tumor

Six ddY male mice each having a weight of about 20 g were used for each group as test animals, and $5 \times 10^6$ Sarcoma 180 tumor cells were implanted subcutaneously into the animals at the axilla. Every 24 hours on days 1 through 5 (relative to tumor implantation), 0.2 ml of a phosphate buffer saline (hereinafter referred to as PBS) containing DC-107 at the concentration shown in Table B was intraperitoneally administered 5 times.

As a control, 0.2 ml of PBS was intraperitoneally administered.

The composition of PBS was 0.8 g/dl NaCl, 0.02 g/dl KCl, 1.15 g/dl $Na_2HPO_4$ and 0.02 g/dl $KH_2PO_4$ (pH 7.2). For comparison, 0.2 ml of PBS containing mitomycin C was intraperitoneally administered 24 hours after implantation of the tumor cells.

Ten days after the implantation, the average tumor volume ($mm^3$) and T/C [T: average tumor volume ($mm^3$) of the groups treated with the test compound, C: that of control $mm^3$)] were measured.

The results are shown in Table 3.

TABLE 3

| Test Compound | Dose (mg/kg) | Average Tumor Volume (mm³) | T/C |
|---|---|---|---|
| DC-107 | 3.1 | 965.8 | 0.49 |
| | 1.6 | 1228.3 | 0.63 |
| | 0 (Control) | 1953.6 | — |
| Mytomycin C | 6 | 437.2 | 0.41 |

(2) Therapeutic effect against lymphocytic leukemia P388

Five male $CDF_1$ mice each having a weight of about 22 g were used for each group as test animals, and $1 \times 10^6$ cells of lymphocytic leukemia P388 tumor cells were implanted intraperitoneally into the test animals. Every 24 hours on days 1 through 5 (relative to tumor implantation), 0.2 ml of PBS containing DC-107 was intraperitoneally administered 5 times. As a control, 0.2 ml of PBS was intraperitoneally administered. For comparison, 0.2 ml of PBS containing mitomycin C was intraperitoneally administered 24 hours after implantation of the tumor cells.

The mean survival time (MST) after implantation and increased life span (ILS) represented by T/C [T: MST of the groups treated with the test compound, C: that of control] are shown in Table 4.

TABLE 4

| Test Compound | Dose (mg/kg) | MST (days) | ILS (T/C) |
|---|---|---|---|
| DC-107 | 3.1 | 17.0 | 1.67 |
| | 1.6 | 15.2 | 1.49 |
| | 0 (Control) | 10.2 | — |
| Mytomycin C | 4 | 18.4 | 1.88 |

DC-107 can be produced by the process described below.

DC-107 can be obtained by culturing a DC-107-producing strain belonging to the genus Streptomyces in a nutrient medium until DC-107 is ted in the culture and recovering DC-107 from the culture.

Any microorganism may be used as long as it belongs to the genus Streptomyces and is capable of producing DC-107. Further, some mutant strains derived from such strains by artificial mutation such as ultraviolet irradiation, X-ray irradiation and treatment with mutagens or by spontaneous mutation have been found to be capable of producing DC-107 and can also be used in the present invention. A preferred example is *Streptomyces atroolivaceus* DO-107 strain isolated by the present inventors from a soil sample obtained in Tsunogun, Yamaguchi Prefecture, Japan.

Characteristics of DO-107 strain with respect to cell components, morphology, cultural characteristics and physiological properties, and identification of the genus and species of the strain are described below. Identification of the strain was made according to the procedures recommended by International Streptomyces Project (ISP) for characterization of species belonging to the genus Streptomyces [E.B. Shirling and D. Gottlieb: Int. J. Syst. Bacteriol., 16, 313–340 (1966)]. The steric configuration of diaminopimelic acid in the whole cell hydrolyzate was determined by the method of B. Becker, et al. [Appl. Microbiol., 12, 421–423 (1964)]. Morphological study was made by using an optical microscope, and a scanning electron microscope was employed for observing the morphology of spore surface. The color indications are given according to the classification in the Color Harmony Manual (Container Corporation of America, 4th edition, 1958). Microbiological properties of DO-107 strain are as follows.

(1) Morphology

Aerial mycelium: It is branched but not fragmented.
Substrate mycelium: It is branched but not fragmented.
Spore Long flexuous or open spiral chains of more than 10 spores are formed at the end of simply branched aerial mycelium.
Surface of spore: Smooth
Motility of spore: No movement observed.

Shape and size of spore: Oval (0.5 to 0.6×0.7 to 0.9 μm)

Formation of sclerotium and sporangium is not observed.

(2) Color

Aerial mycelium: Gray or white
Substrate mycelium: Pale yellow to yellow brown
Soluble pigment: No pigment formed.

(3) Chemical composition of cell wall

Steric configuration of diaminopimelic acid: LL-form (4) Physiological properties Assimilability of carbon sources:
  Assimilable: Glucose, arabinose, xylose, inositol, mannitol, fructose, rhamnose, raffinose
  Nonassimilable: Sucrose
Melanin-like pigment: Negative
Liquefaction of gelatin: Negative
Hydrolysis of starch: Negative
Coagulation and peptonization of defatted milk: Both negative
Decomposition of cellulose: Positive
Growth temperature range: 15 to 33° C. (optimum: 28 to 30° C.)

Growth temperature range was determined after two days of culturing, the actions upon gelatin, defatted milk and cellulose were observed after one month of culturing at 28° C., and the other observations were made after two weeks of culturing at 28° C.

(5) Cultural characteristics on various agar media

Cultural characteristics of DO-107 strain on various agar media observed after culturing at 28° C. for 28 days are shown in Table 5.

TABLE 5

| Medium | Cultural Characteristics |
|---|---|
| Sucrose-nitrate agar medium | G: Good<br>AM: Fair, natural (2dc)<br>SM: Cobalt gray (2fe) to putty (1dc) |
| Glucose-asparagine agar medium | G: Moderate<br>AM: Fair, pearl (2ba)<br>SM: Light ivory (2ca) |
| Glycerol-asparagine agar medium | G: Good<br>AM: Abundant, cobalt gray (2fe) to yellow tint (1ba)<br>SM: Bisque (2ec) to light ivory (2ca) |
| Starch agar medium | G: Good<br>AM: Abundant, cobalt gray (2fe) to natural (2dc)<br>SM: Light ivory (2ca) to bisque (2ec) |
| Tyrosine agar medium | G: Good<br>AM: Abundant, natural (2dc) to cobalt gray (2fe)<br>SM: Bisque (2ec) to bamboo (2gc) |
| Nutrient agar medium | G: Moderate<br>AM: Fair, yellow tint (1ba)<br>SM: Light ivory (2ca) |
| Yeast extract-malt extract agar medium | G: Good<br>AM: Fair, dark cobalt gray (2ih)<br>SM: Mustard tan (21g) to bamboo (2gc) |
| Oatmeal agar medium | G: Extremely good<br>AM: Abundant, silver gray (3fe) to white (a)<br>SM: Bisque (2ec) |
| Peptone-yeast extract-iron agar medium | G: Poor<br>AM: None<br>SM: Light wheat (2ea) |
| Hickey-Tresner agar medium | G: Good<br>AM: Abundant, silver gray (3fe)<br>SM: Beige brown (3ig) |

Formation of soluble pigment was not observed on any of the culturing media. Abbreviations are as follows. G: degree of growth, AM: formation of aerial mycelium and its color, SM: color of substrate mycelium.

(6) Identification of DO-107 strain

DO-107 strain belongs to the Type I cell wall group according to the classification of Lechevalier and Lechevalier [M.P. Lechevalier and H.A. Lechevalier: Int. J. Syst. Bacteriol., 20, 435–443 (1970)], since LL-diaminopimelic acid is contained in the whole cell hydrolyzate. On the basis of this characteristic and morphological characteristics, this strain should reasonably be designated as a strain of the genus Streptomyces.

A search was made through the Approved Lists of Bacterial Name of International Code of Nomenclature of Bacteria [V.B.V. Skerman, et al., Int. J. Syst. Bacteriol., 0, 225–420 (1980)], for a strain having microbiological properties akin to those of DO-107 according to the descriptions of ISP (Int. J. Syst. Bacteriol , 18, 69–189 (1968), ibid., 18, 279–392 (1968), ibid., 19, 391–512 (1969) and ibid., 22, 265–394 (1972)].

Keys for the search are as follows:
Gray aerial mycelium
Flexuous or open spiral spore chains
Smooth spore surface
No formation of either melanin-like pigment or soluble pigment
Assimilation patterns of carbon sources As a result of the search, Streptomyces mirabilis and Streptomyces atroolivaceus were selected.

Comparison in more detail revealed that Streptomyces mirabilis is markedly different from DO-107 strain in that the substrate mycelium shows a grayish blue or grayish green color on yeast extract-malt extract agar medium. On the other hand, Streptomyces atroolivaceus is different from DO-107 strain in that its growth is weak on medium of ISP9, but taxonomical characteristics of the strain were otherwise closely agreed with those of DO-107 strain. Therefore, DO-107 strain was identified to be Streptomyces atroolivaceus, named S. atroolivaceus DO-107, and deposited with the Fermentation Research Institute, Agency of Industrial Science and Technology, Japan under FERM BP-1405 on July 4, 1987.

For the culturing of the strain of the present invention, conventional methods for culturing Actinomycetes are generally used. As the medium, either a natural medium or synthetic medium can be employed so long as it contains proper amounts of assimilable carbon sources, nitrogen sources, inorganic matters, etc. As the carbon source, glucose, starch, glycerol, mannose, fructose, sucrose, molasses, etc. can be used either alone or in combination. Hydrocarbons, alcohols, organic acid, etc. can also be used depending on the assimilability of the strain. As the nitrogen source, inorganic or organic nitrogen-containing compounds such as ammonium chloride, ammonium sulfate, ammonium nitrate, sodium nitrate, and urea, and natural nitrogenous substances such as peptone, meat extract, yeast extract, dry yeast, corn steep liquor, soybean meal and Casamino acid can be used either alone or in combination. As the inorganic matters, inorganic salts such as sodium chloride, potassium chloride, ferrous sulfate, magnesium sulfate, zinc sulfate, manganese sulfate, copper sulfate, calcium carbonate, phosphates, etc. can be used. If necessary, organic or inorganic substances capable of promoting the growth of the strain used and its production of DC-107 such as biotin and vitamins, can be appropriately employed.

Culturing may be carried out by liquid culture or solid culture, but is usually carried out by liquid culture, and most preferably by submerged culture with stirring.

Culturing temperature is 20 to 30° C., preferably 23 to 28° C. It is desirable to maintain the pH of the medium at 4 to 10, preferably 5 to 7 by the addition of aqueous ammonia or aqueous ammonium carbonate during the culturing.

Usually after one to seven days of liquid culture, the desired substance is formed and accumulated in the culture liquor and microbial cells. Culturing is discontinued when the amount of the product in the culture reaches the maximum. Then, the product is isolated and purified from the culture.

Isolation and purification of DC-107 are carried out by the methods usually used for isolation and purification of microbial metabolites from culture. For example, the culture is separated into culture filtrate or supernatant and microbial cells by filtration, centrifugation, etc. The microbial cells are extracted with a suitable solvent which can dissolve this substance such as methanol and acetone. The extract is concentrated under reduced pressure to remove the solvent and the concentrate is then dissolved in water to make an aqueous solution. The solution is combined with the culture filtrate or supernatant, and the combined solution is treated with a non-ionic porous resin such as Diaion HP-20 (Mitsubishi Chemical Industries, Ltd.) to absorb the active component. Then, the absorbed active component is eluted with a suitable solvent such as methanol and acetone. The eluate is concentrated and purified using silica gel (Wakogel C-200, Wako Pure Chemical Industries, Ltd.), etc. The product is further purified using silica gel (Lichroprep Si60, Merck Inc.), etc. and then using reversed phase type silica gel (Wakogel-L.C-ODS, Wako Pure Chemical Industries, Ltd.), etc. to obtain DC-107.

The purity of the thus obtained DC-107 can be further raised by procedures such as recrystallization and high performance liquid chromatography.

During the cultivation and purification steps, DC-107 can be traced by bioassay using *Bacillus subtilis* No. 10707, or by measuring UV absorption of thin layer chromatograms.

DC-107 can be used as an antibiotic and an anti-tumor agent in suitable dosage forms prepared by combination with at least one pharamaceutical diluent, adjuvant or carrier. For example, DC-107 is usually dissolved in physiological saline, glucose solution, lactose solution or mannitol solution to prepare injections for intraveneous administration. It may also be administered intraarterially, intraperioneally or intrathoracically in similar doses. Freeze-drying according to the method specified in Pharamacopoeia of Japan may be applied to solutions containing DC-107, and injectable powder can be prepared by adding sodium chloride. The pharmaceutical preparations of this compound may also contain pharmaceutically acceptable well-known diluents, adjuvants and/or carriers such as pharmaceutically acceptable salts. When DC-107 is used as an injection, it is preferable, in some cases, to use an additive that enhances the solubility of this active ingredient, for example, HCO60 and PEG. It may also contain a carrier such as liposome and lipid emulsion. Doses of DC-107 may be adjusted appropriately depending on the age and conditions of patients. Administration schedule may also be adjusted depending on the dose, as well as the age and conditions of patients; for example, DC-107 may be intermittently administered every several hours, once a week or once every three weeks, or successively administered once a day. DC-107 may also be orally or rectally administered in similar doses and in the similar manner. For oral or rectal administration, it is used in the form of tablets, powder, granules, syrup or suppository with conventional adjuvants.

Certain specific embodiments of the present invention are illustrated by the following representative example and reference examples.

EXAMPLE

*Streptomyces atroolivaceus* DO-107 was used as the seed strain. One loopful of the strain was inoculated into 50 ml of a seed medium having the following composition in a 300 ml-Erlenmeyer flask and subjected to shaking culture (200 rpm) at 28° C. for 48 hours.

Composition of the seed medium: 10 g/l glucose, 10 g/l soluble starch, 5 g/l Bacto-Tryptone, 5 g/l yeast extract, 3 g/l beef extract, an 2 g/l calcium carbonate (pH 7.2 prior to sterilization).

The resulting seed culture was inoculated into 18 l of a fermentation medium having the following composition in a 30 l-jar fermentor in a ratio of 5% by volume and cultured with agitation and aeration (350 rpm, 18 l/min) at 25° C.

Composition of the fermentation medium: 50 g/l soluble starch, 30 g/l corn steep liquor, 0.5 g/l $KH_2PO_4$, 0.5 g/l $MgSO_4.7H_2O$, and 5 g/l calcium carbonate (pH 7.0, adjusted with NaOH prior to sterilization).

Culturing was carried out for 72 hours without controlling the pH of the medium.

Then, 15 l of the culture was adjusted to pH 5 with 6N HCl, and separated into filtrate and microbial cells by filtration. Ten liters of methanol was added to the microbial cells, and after thorough stirring, the cells were removed by filtration. The thus obtained methanol extract (10l) was combined with the filtrate. After the pH was adjusted to 4 with 4N HCl, the solution was passed through 1.2l of the nonionic porous resin Diaion HP-20 (Mitsubishi Chemical Industries, Ltd.). The column was washed with 50% methanol containing 0.2% acetic acid to remove impurities and eluted with 100% methanol containing 0.2% acetic acid to obtain active fractions. The eluted fractions were diluted with an equal amount of deionized water and passed through the nonionic porous resin Diaion HP-20SS (Mitsubishi Chemical Industries, Ltd.) to absorb the active component. After washing the 50% methanol containing 0.2% acetic acid, elution was carried out with the above solvent system in which the rate of methanol was increased stepwise. The active component was eluted in the fractions containing about 85% methanol. The active fractions were concentrated and extracted with ethyl acetate. After dehydration over sodium sulfate, the extract was concentrated and the concentrate was applied to a column packed with silica gel (BW300, Fuji Devision Chemical Co., Ltd.), followed by elution with a mixed solvent of n-hexane, ethyl acetate and acetic acid (5:5:0.1 by volume). The eluate thus obtained was concentrated, whereby about 400 mg of brown powder was obtained. The powder was applied to a silica gel column (Lichroprep Si60, Merck Inc.) and elution was carried out with a mixed solvent of chloroform and methanol (50:1 by volume) under a pressure of about 10 $kg/cm^2$. The eluted active fractions were concentrated and applied to a reversed phase type silica gel column (YMC gel, Yamamura Chemical Research Laboratories). Then, density gradient elution was carried out with methanol solution containing 0.2% acetic acid in which the rate of methanol was increased stepwise from 40% to 80%. The active fractions were concentrated and extracted with ethyl acetate. The extract was concentrated, and crystallization of the residue from chloroform was carried out to obtain 50 mg of DC-107 as white needles.

The thus obtained DC-107 showed the physicochemical properties and biological properties described above.

REFERENCE EXAMPLE 1

Injection

DC-107 (10 mg) was dissolved in 50 ml of ethanol, and after stirring, ethanol was removed under reduced pressure. The residue thus obtained was dissolved in about 10 ml of sterile physiological saline solution to obtain injections.

REFERENCE EXAMPLE 2

Tablet

Tablets were prepared from 10 mg of DC-107, 200 mg of lactose, 40 mg of corn starch, 4 mg of polyvinyl alcohol, 28 mg of Avicel and 1 mg of magnesium stearate.

What is claimed is:

1. A compound DC-107 having the following physicochemical properties:
    (1) molecular formula: $C_{22}H_{26}N_2O_6S_3$
    (2) molecular weight: 510
        found by high resolution FAB mass spectrum: 511.1041
        calculated for $C_{22}H_{27}N_2O_6S_3$: 511.1031
    (3) melting point: 160° C. (decomposed)
    (4) specific rotation: $[\alpha]^{25}_D = 140°$ (c=0.1, methanol)
    (5) ultraviolet absorption spectrum: as shown in FIG. 1
    (6) infrared absorption spectrum: as shown in FIG. 2
    (7) solubility:
        soluble in methanol, ethyl acetate, chloroform and acetone,
        insoluble in water and n-hexane
    (8) color reaction:
        positive in reactions with ninhydrin, p-anisidine and Ehrlich's reagent
    (9) a white, neutral substance
    (10) $^1$H-NMR spectrum (400 MHz, in DMSO-$d_6$, internal standard TMS): as shown in FIG. 3
    (11) $^{13}$C-NMR spectrum (100 MHz, in DMSO-$d_6$, internal standard TMS): as shown in FIG. 4.

2. A process for producing DC-107 which comprises culturing in a medium a microorganism belonging to the genus Streptomyces and capable of producing DC-107 until a substantial amount of DC-107 is accumulated in the culture and recovering DC-107 therefrom.

3. The process according to claim 2, wherein the microorganism is *Streptomyces atroolivaceus* DO-107 (FERM BP-1405).

4. A pharmaceutical composition comprising a pharmaceutical carrier and an effective antibacterial amount of DC-107 defined in claim 1.

5. A compound having the structural formula

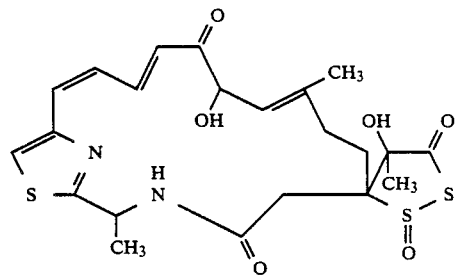

* * * * *

UNITED STATES PATENT AND TRADEMARK OFFICE
CERTIFICATE OF CORRECTION

PATENT NO. : 4,999,196
DATED : March 12, 1991
INVENTOR(S) : HIROFUMI NAKANO, ET AL.          Page 1 of 2

It is certified that error appears in the above-identified patent and that said Letters Patent is hereby corrected as shown below:

COLUMN 2

Line 13, "TMS)" should read --TMS):--.
    Line 15, "TMS)" should read --TMS):--.
    Line 17, "$R_4$ values" should read --$R_f$ values--.
    Line 41, "sue" should read --use--.
    Lines 66-67, delete "However, although amplitudes can be measured experimentally using x-ray all the atoms in a crystal lattice."

COLUMN 3

Line 45, "Table B" should read --Table 3--.

COLUMN 4

Line 29, "ted" should read --accumulated--.
    Line 64, "Spore" should read --Spore:--.

COLUMN 6

Line 5, "Bacteriol ," should read --Bacteriol.,--.
    Line 15, "Bacteriol ," should read --Bacteriol.,--.

UNITED STATES PATENT AND TRADEMARK OFFICE
CERTIFICATE OF CORRECTION

PATENT NO. : 4,999,196
DATED : March 12, 1991
INVENTOR(S) : HIROFUMI NAKANO, ET AL.

Page 2 of 2

It is certified that error appears in the above-identified patent and that said Letters Patent is hereby corrected as shown below:

COLUMN 8

Line 33, "was" should read --were--.
    Line 38, "nonionic" should read --non-ionic--.
    Line 45, "nonionic" should read --non-ionic--.
    Line 46, "absorb" should read --adsorb--.
    Line 56, "Devision" should read --Division--.

Signed and Sealed this

Thirteenth Day of October, 1992

Attest:

DOUGLAS B. COMER

*Attesting Officer*      Acting Commissioner of Patents and Trademarks